(12) United States Patent
Lee et al.

(10) Patent No.: US 7,585,465 B2
(45) Date of Patent: Sep. 8, 2009

(54) PHARMACEUTICAL PRODUCT RELEASE RATE TESTING DEVICE

(75) Inventors: Luke Lee, Belle Mead, NJ (US); Yu Sheng Zhang, Stewartsville, NJ (US); Jose Castro, Garfield, NJ (US)

(73) Assignee: Logan Instruments Corp., Somerset, NJ (US)

( * ) Notice: Subject to any disclaimer, the term of this patent is extended or adjusted under 35 U.S.C. 154(b) by 339 days.

(21) Appl. No.: 11/453,634

(22) Filed: Jun. 15, 2006

(65) Prior Publication Data

US 2007/0292309 A1    Dec. 20, 2007

(51) Int. Cl.
*G01N 33/48* (2006.01)
*B01F 9/08* (2006.01)
*B01F 15/06* (2006.01)

(52) U.S. Cl. .......................... 422/68.1; 422/64; 366/91; 366/142; 366/143; 366/145; 366/297; 73/866

(58) Field of Classification Search .................. None
See application file for complete search history.

(56) References Cited

U.S. PATENT DOCUMENTS

| | | | |
|---|---|---|---|
| 3,807,353 A * | 4/1974 | Kobernick | 118/702 |
| 4,879,917 A * | 11/1989 | Eppelmann et al. | 73/866 |
| 4,924,716 A * | 5/1990 | Schneider | 73/866 |
| 5,011,662 A * | 4/1991 | Noormohammadi et al. | 422/68.1 |
| 5,682,001 A | 10/1997 | Hanson et al. | |
| 5,796,016 A | 8/1998 | Muller | |
| 6,060,024 A | 5/2000 | Hutchins et al. | |
| 6,163,149 A | 12/2000 | Loffler | |
| 6,170,980 B1 | 1/2001 | Martin | |
| 6,174,497 B1 | 1/2001 | Roinestad et al. | |
| 6,497,157 B1 | 12/2002 | Viegas et al. | |
| 6,727,480 B2 | 4/2004 | Fernando et al. | |
| 6,929,782 B1 | 8/2005 | Ciliberto et al. | |
| 6,948,389 B2 * | 9/2005 | Brinker et al. | 73/863.01 |
| 6,962,674 B2 | 11/2005 | Dean et al. | |
| 2004/0168529 A1 | 9/2004 | Carlson et al. | |
| 2005/0166688 A1 | 8/2005 | Tian et al. | |
| 2005/0207941 A1 * | 9/2005 | Lee et al. | 422/82 |
| 2005/0238540 A1 | 10/2005 | Swon et al. | |
| 2006/0260421 A1 * | 11/2006 | Sekizawa et al. | 73/866 |
| 2007/0196238 A1 * | 8/2007 | Kennedy et al. | 422/68.1 |

* cited by examiner

*Primary Examiner*—Jill Warden
*Assistant Examiner*—P. Kathryn Wright
(74) *Attorney, Agent, or Firm*—Brian Roffe (57) ABSTRACT

Pharmaceutical product release rate testing device includes a base, at least one carousel member rotatably mounted on the base, each carousel member including a plurality of test tube pockets each adapted to receive a test tube fillable with test media, and a dipping mechanism for dipping samples to be tested into the test tubes when present in the pockets and filled with test media. A rinsing/filling mechanism is provided to rinse or fill test tubes in one set of pockets while test tubes in another set of pockets are involved in the dipping process via the dipping mechanism. The carousel member is temperature-controlled such that all of the test tubes when present in the pockets are at substantially the same temperature for critical stages of the testing process. Methods for conducting pharmaceutical product release rate testing using the device are also disclosed.

16 Claims, 4 Drawing Sheets

PHARMACEUTICAL PRODUCT RELEASE RATE TESTING DEVICE

FIELD OF THE INVENTION

The present invention relates to a device for testing the release rate of pharmaceutical products, in particular, drugs.

The present invention also relates to a pharmaceutical product release rate testing system and method using the device.

BACKGROUND OF THE INVENTION

Release rate testing of drugs is often a very tedious job, partly because samples of the drug must be released in different media and also because the temperature of test tubs containing the different media must be accurately controlled. One traditional way to perform drug release rate testing is to prepare the different media in a number of test tubes and set the test tubes into a water bath or similar water-containing vessel which maintains the test tubes at a predetermined, desired temperature. One current apparatus used in drug release rate testing enables the test tubes to be set in several rows with twelve test tubes per row, with each row of test tubes being filled with fresh media. A motor-driven bar holding twelve sample holders, each containing a sample of the drug being tested, dips the sample holders into a row of twelve test tubes. The sample holders are sequentially dipped into test tubes in each row until the test is complete.

One drawback of this type of apparatus is that some drugs must test for twenty rows, i.e., be dipped into media in twenty test tubes each in one of twenty rows of such test tubes, which results in the test apparatus being large and long, and also requiring a relatively large water tank to hold the warm water to provide for the temperature-controlled water bath. Such an apparatus wastes a considerable amount of energy for testing twelve samples. Space is another problem since more test rows required more bench space.

Another problem concerns the filling of the test media into the test tubes. Since the test media is typically capable of evaporating and any such evaporation may adversely affect the test conditions, the media can only be filled into the test tubes a few minutes before the test, i.e., before the sample holder with the sample of the drug being tested is inserted therein, to avoid evaporation of even a small volume of the test media. Moreover, the test media must be removed from the test tubes and the test tubes cleaned after each test. Before removing the test media, at least some of the test media must be removed from each test tube for analysis. Such an apparatus occupies a relatively large amount of space and wastes energy, and also requires several people to work around it for the release rate test.

OBJECTS AND SUMMARY OF THE INVENTION

It is an object of the present invention to provide a new and improved device for testing the release rate of pharmaceutical products, in particular, drugs.

It is another object of the present invention to provide a new and improved method for testing the release rate of pharmaceutical products.

It is yet another object of the present invention to provide a new and improved drug release rate testing device and method in which test tubes are temperature-controlled in a more efficient and economical manner than in prior art drug release rate testing apparatus.

It is yet another object of the present invention to provide a new and improved drug release rate testing device and method in which test tubes into which sample holders containing samples to be tested are all maintained at a substantially uniform temperature.

It is still another object of the present invention to provide a new and improved drug release rate testing device and method in which sample holders can be dipped into test media in test tubes while simultaneously other test tubes can be prepared for a subsequent test.

Still another object of the present invention is to provide a new and improved drug release rate testing device and method in which both a dipping mechanism for dipping sample holders into test tubes and a filling and rinsing mechanism for filling test tubes with media and rinsing used test media out of the test tubes are mounted on a common structure or lab bench with the test tubes being moved to alternatingly be operated upon by the dipping mechanism or the filling and rinsing mechanism.

In order to achieve these objects and others, a first embodiment of a drug release rate testing device in accordance with the invention includes a base, at least one carousel member rotatably mounted on the base, each carousel member including a plurality of test tube pockets each adapted to receive a test tube fillable with test media, and a dipping mechanism for dipping samples of the pharmaceutical product to be tested into the test tubes when present in the test tube pockets and filled with test media.

By providing a rotatable carousel member, or any other type of rotatable test tube retaining member, significant advantages are obtained. For example, test tube in one set of pockets on one side of the carousel member can be in operative relationship with one type of test apparatus, e.g., the dipping mechanism, whereas test tubes in another, different set of pockets on another side of the carousel member can be in operative relationship with a different type of test apparatus, e.g., a rinsing/filling mechanism. It thus becomes possible to simultaneously perform dipping of samples of the pharmaceutical product into media in test tubes and rinsing and filling of other test tubes for subsequent dipping of the same samples. The subsequent dipping is obtained simply by rotating the carousel member from a position in operative relationship with the dipping mechanism to a position in operative relationship with the rinsing/filling mechanism. Rotation of the test tubes between the two positions is controlled as desired, i.e., as per the requirements of the test being performed. This significantly expedites the testing process and saves a lot of preparation time.

In a preferred embodiment, the carousel member is temperature-controlled such that all of the test tubes when present in the test tube pockets are at substantially the same temperature. This avoid the problem of inconsistently heated test tubes as well as dipping being performed at inappropriate temperatures.

Each carousel member may have a substantially cylindrical form and defines the pockets on an outer periphery. To optimize use of the dipping mechanism and the rinsing/filling mechanism, it is preferred that each set of pockets extends over half of the periphery of the carousel member, i.e., a 180° segment. A carousel rotation mechanism rotating each carousel member such that each set of pockets is alternatingly in alignment with the dipping mechanism and in alignment with the filling/rinsing mechanism.

A movement coordinating or linking mechanism can be provided for linking vertical movement of the dipping mechanism and vertical movement of the filling/rinsing mechanism.

An actuating mechanism can be provided for vertically moving the dipping system between different vertical positions including a position in which the samples to be tested are dipped into the test tubes when present in the pockets and filled with test media and a position in which the samples are over the carousel member(s) to enable the carousel member(s) to be rotated.

Another embodiment of a drug release rate testing device in accordance with the invention includes a base, at least one carousel member rotatably mounted on the base, each carousel member including a plurality of test tube pockets each adapted to receive a test tube fillable with test media, a dipping arm coupled to the base and movable vertically relative to the carousel member(s), the dipping arm including structure to enable samples of the pharmaceutical product being tested to be dipped into test tubes when present in a first set of the pockets and filled with test media, and a filling/rinsing arm coupled to the base and movable vertically relative to the carousel member(s). The filling/rinsing arm includes structure for rinsing test tubes when present in a second set of the pockets and filling test tubes with test media when present in the second set of the pockets. The first and second sets of pockets are different than one another such that both dipping of samples and rinsing or filling of test tubes can be performed simultaneously. However, simultaneous dipping and rinsing or filling is not required and the test tubes can be filled or rinsed before or after the dipping.

The variations of the release rate testing device described above can be applied to this device as well, to the extent possible.

Another embodiment of a drug release rate testing device in accordance with the invention includes a base, at least one test tube retaining member mounted on the base, each test tube retaining member including a plurality of test tube pockets each adapted to receive a test tube fillable with test media and which is temperature-controlled such that all of the test tubes when present in the pockets are at substantially the same temperature, and a dipping mechanism for dipping samples of the pharmaceutical product to be tested into the test tubes when present in the pockets and filled with test media. In this embodiment, the test tube retaining member is not required to be a rotatable carousel member as described above. Rather, any retaining member which is temperature-controlled is usable. Temperature-control involves use of a heating system and a temperature sensor which is monitored by a controller which controls the heating system to ensure the test tubes are at a substantially uniform temperature at critical stages in the testing process.

The variations of the release rate testing device described above can be applied to this device as well, to the extent possible.

Other and further objects, advantages and features of the present invention will be understood by reference to the following specification in conjunction with the annexed drawings.

BRIEF DESCRIPTION OF THE DRAWINGS

The invention, together with further objects and advantages thereof, may best be understood by reference to the following description taken in conjunction with the accompanying drawings wherein like reference numerals identify like elements.

DETAILED DESCRIPTION OF THE INVENTION

Figure 1:
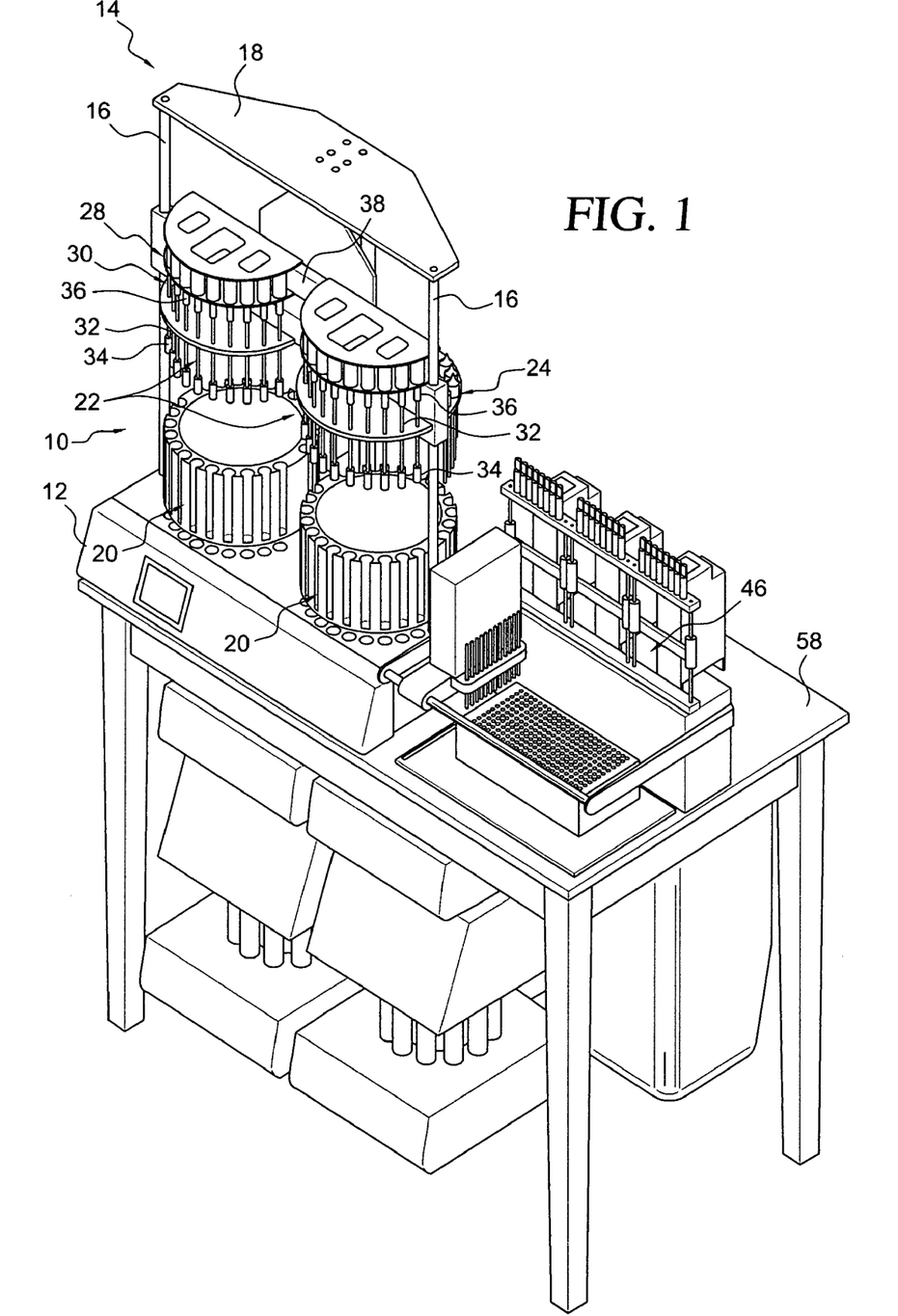
FIG. 1 is a front perspective view of the drug release rate testing device in accordance with the invention on a lab bench and in a position in which a carousel member is rotatable.
Figure 2:
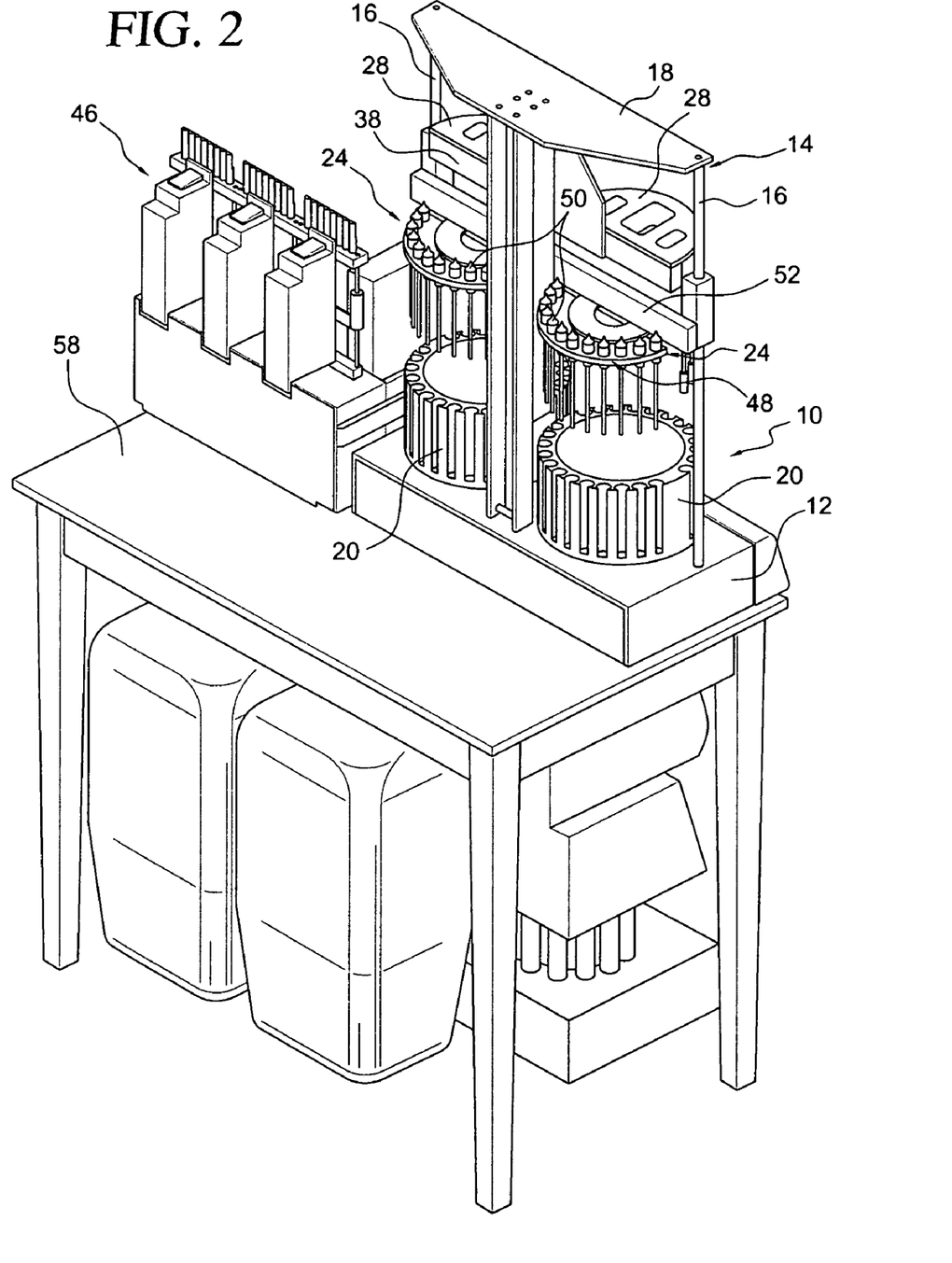
FIG. 2 is a rear perspective view of the drug release rate testing device shown in FIG. 1 in the position in which the carousel member is rotatable.
Figure 3:
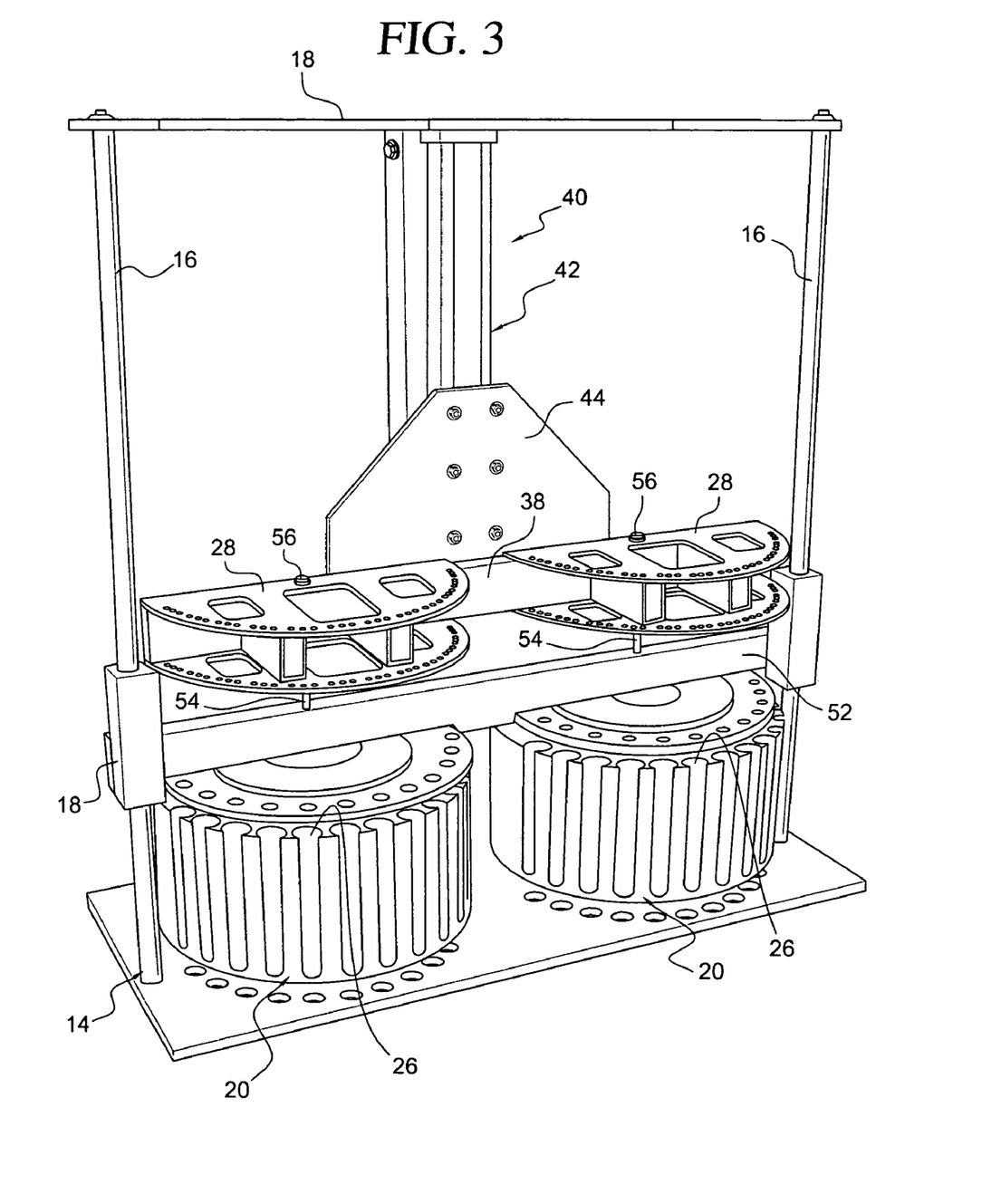
FIG. 3 is an enlarged view of parts of the drug release rate testing device shown in FIGS. 1.

Referring to the accompanying drawing, a drug release rate testing device in accordance with the invention is designated generally as 10 and comprises a base 12, a support system 14 including support rods 16 extending vertically upward from the base 12 and a cross member 18 extending between the rods 16 at a vertical elevation above the base 12, and a pair of carousel members 20 rotatably mounted on the base 12 (see FIGS. 1 and 2). Device 10 also includes a pair of dipping systems 22 arranged on one side of the support system 14 and a pair of filling/rinsing systems 24 arranged on an opposite side of the support system 14, each dipping system 22 and each filling/rinsing system 24 is operative on a respective one of the carousel members 20 in a manner described below.

Each carousel member 20 has a substantially cylindrical form, optionally with a hollow interior, and is rotatably mounted to the base 12 in any manner known to those skilled in the art of rotational mounting of one member relative to another member. In the illustrated embodiment, each carousel member 20 includes twenty-four test tube receptacles or pockets 26 each capable of receiving and securely retaining a single test tube. Pockets 26 are arranged around an outer periphery of the carousel member 20. Nevertheless, the invention also contemplates carousel members with different numbers of test tube pockets and arranged in different locations about the carousel member.

Test tube pockets 26 are optimally designed to accommodate a standard size test tube used in pharmaceutical product testing. Test tube pockets 26 are preferably grouped together in two groups with each group being alternatingly in operative relationship with the dipping system 22 and the filling/rinsing system 24. Thus, when one group of test tube pockets 26 is in operative relationship with the dipping system 22 (referred to as being in the dipping station), the other group of test tube pockets is in operative relationship with the filling/rinsing system 24 (referred to as being in the filling/rinsing station).

Each carousel member 20 is also provided with a temperature-controlled heating system (not shown in FIGS. 1 and 2) which controls the temperature of all of the test tubes when received in the test tube pockets 26, to ensure that all of the test tubes are tested at the same, uniform temperature. In view of the presence of the temperature-controlled heating system common to all of the test tubes, the traditional water bath design in conventional drug release rate testing devices is neither present nor required.

Each carousel member 20 can also be provided with a locking mechanism controlled by the control system of the device 10. Such a locking mechanism may be arranged partially or entirely inside each carousel member 20 and ensures that the carousel members 20 are secured or fixed in position in each of the dipping station and the filling/rinsing station and do not unintentionally rotate during the dipping, rinsing and filling stages.

The design of the temperature-controlled heating system could be any type or combination of types of heating systems. Examples includes a heating system in which the carousel members 20 themselves are heated, and a heating system in which heat is directed specifically to the pockets 26 defined by the carousel members 20 to operatively heat test tubes therein. The heating system can be arranged in the base 12 underneath each carousel member 20. A temperature sensor system is included in or associated with the heating system to enable the temperature of the test tubes to attain a desired temperature.

Each dipping system 22 includes a semi-circular sample holder retaining member 28 to which twelve dipping bars 30 are mounted. Each dipping bar 30 includes a shaft 32 attached to the sample holder retaining member 28 and which passes through an aperture in a tube cover 34. A sample probe 36 is operatively mounted on shaft 32. Tube cover 34 is designed to cover the test tubes when placed in the carousel member 20 when the sample probes 36 are situated in the test tubes. The sample holder retaining members 28 are mounted to a movable cross member 38.

Dipping systems 22 are mounted to an actuating mechanism 40 which moves the dipping systems 22 up and down relative to the carousel members 20 by moving the cross member 38 up and down. Actuating mechanism 40 includes an upright support 42, a plate 44 connected to the cross member 38 and a movement mechanism (not shown) arranged in connection with the support 42 and the plate 44 to cause movement of the plate 44 up and down relative to the support 42. The structure of such a movement mechanism is readily ascertainable to one of ordinary skill in the art.

The combination of the dipping systems 22, cross member 38 and plate 44 serves as a dipping arm which is moved up and down to cause the sample probes 36 to be dipped into the fluid in the test tubes or removed therefrom.

Dipping systems 22 are connected to a sample collector 46 which includes a fluid connection to each dipping shaft 32 to enable a sample of the fluid in the test tube into which the dipping shaft 22 is inserted to be directed to the sample collector 46 for testing. The fluid connections between the sample collector 46 and the dipping systems 22 are not shown in FIGS. 1 and 2. Possible sample collectors for use with device 10 include those designated SCT-90W and SCT-160V/SCT-240V/SCT-480V manufactured by the current assignee, Logan Instruments Corporation.

Each filling/rinsing system 24 includes a semi-circular plate 48 to which twelve delivery nozzles 50 are mounted in positions aligning with the test tube pockets 26 in the carousel members 20, and a cross member 52 having ends with channels which slide along the vertical support rods 16. Vacuum tubes are also connected to the plate 48. Plates 48 are mounted to cross member 52. The combination of cross member 52, plate 48 and delivery nozzles 50 serves as a filling and rinsing arm which is moved up and down to alternatingly rinse the test tubes or fill the test tubes with test media.

Movement coordinating pins 54 are fixed to an upper surface of the cross member 52. Each sample holder retaining member 28 includes a channel in which the pins 54 slide. Pins 54 serve to provide for dependent movement of the dipping arm and filling and rinsing arm, and thus dependent movement of the sample holder retaining members 28 relative to the cross member 52. As such, the movement coordinating pins 54 constitute a mechanism for coordinating or linking vertical movement of the dipping system 22 and vertical movement of the filling/rinsing system 24. Movement of the dipping arm relative to the filling and rinsing arm is limited by stops 56 arranged at the upper ends of the pins 54.

Specifically, when the actuating mechanism 40 moves the cross member 38 with the dipping systems 22 downward, sample holder retaining members 28 contact the cross member 52 and move the cross member 52 downward along the support rods 16. Once the cross member 18 is in a position in which the tube covers 34 cover the test tubes in the carousel members 20 and the delivery nozzles 50 are situated in the test tubes in the filling and rinsing station, the actuating mechanism 40 then moves the cross member 38 up and down along the pins 54 in a reciprocating manner substantially between a position in which the sample holder retaining members 28 approach and possibly contact the cross member 52 and a position in which the sample holder retaining members 28 approach and possibly contact the stops 56.

When the dipping is concluded, the actuating mechanism 40, moves the sample holder retaining members 28 upward against the stops 56 and continues the upward movement causing the cross member 52 to be moved upward, tube covers 34 to be moved apart from the carousel members 20 and the delivery nozzles 50 to be moved out of engagement with the test tubes in the carousel members 20. The timing of the movements of the actuating mechanism 40 and the results thereof are described below when the operation of the device 10 is described.

Filling/rinsing systems 24 are connected to a fluid delivery system such as one designated MDS-1200 manufactured by the current assignee, Logan Instruments Corporation. The fluid delivery system automatically directs a stream of media to the delivery nozzles 50, preferably pre-heated media, such that the test tubes in the test tube pockets 26 in the carousel member 20, when in the filling and rinsing station station, are all quickly and simultaneously filled with media.

As shown in FIGS. 1 and 2, the device 10 is arranged on a lab bench 58 having an approximate size of 30" by 60". Such a lab bench 58 is advantageous for the invention since it can accommodate not only the device 10, but also a sample collector 46 along the device 10 as well as a fluid or media delivery system and fluid rinsing system (or automatic vessel cleaner) which can be operatively attached to the filling/rinsing systems 24. Moreover, tanks for the storage of filling fluids (test media), rinsing fluids and waste fluids, as well as other equipment needed to perform release rate testing can be arranged underneath the lab bench 58.

An automatic vessel cleaner can thus be arranged in the lab bench 58 and include the tanks or reservoirs of rinsing fluid and waste fluids. Such an automatic vessel cleaner would also include a vacuum system for applying a vacuum to the test tubes through, for example, the delivery nozzles 50. A media delivery system can include the tanks or reservoirs of test media or dissolution media. A common pump can be attached to both the automatic vessel cleaner and media delivery system, and to the delivery nozzles 50 or alternatively, delivery nozzles 50 can be attached two pumps, one for pumping dissolution media from the media delivery system into the test tubes and another one for allowing the contents of the test tubes to be vacuumed out and the test tubes rinsed with rinsing fluid. Alternatively, multiple delivery nozzles could be provided.

In the illustrated embodiment of the device in accordance with the invention, there are two carousel members 20. However, a device in accordance with the invention can include only a single carousel member or more than two carousel members. Even if the device includes a plurality of carousel members, it is possible that during use, less than all of the carousel members could be used.

Figure 4:
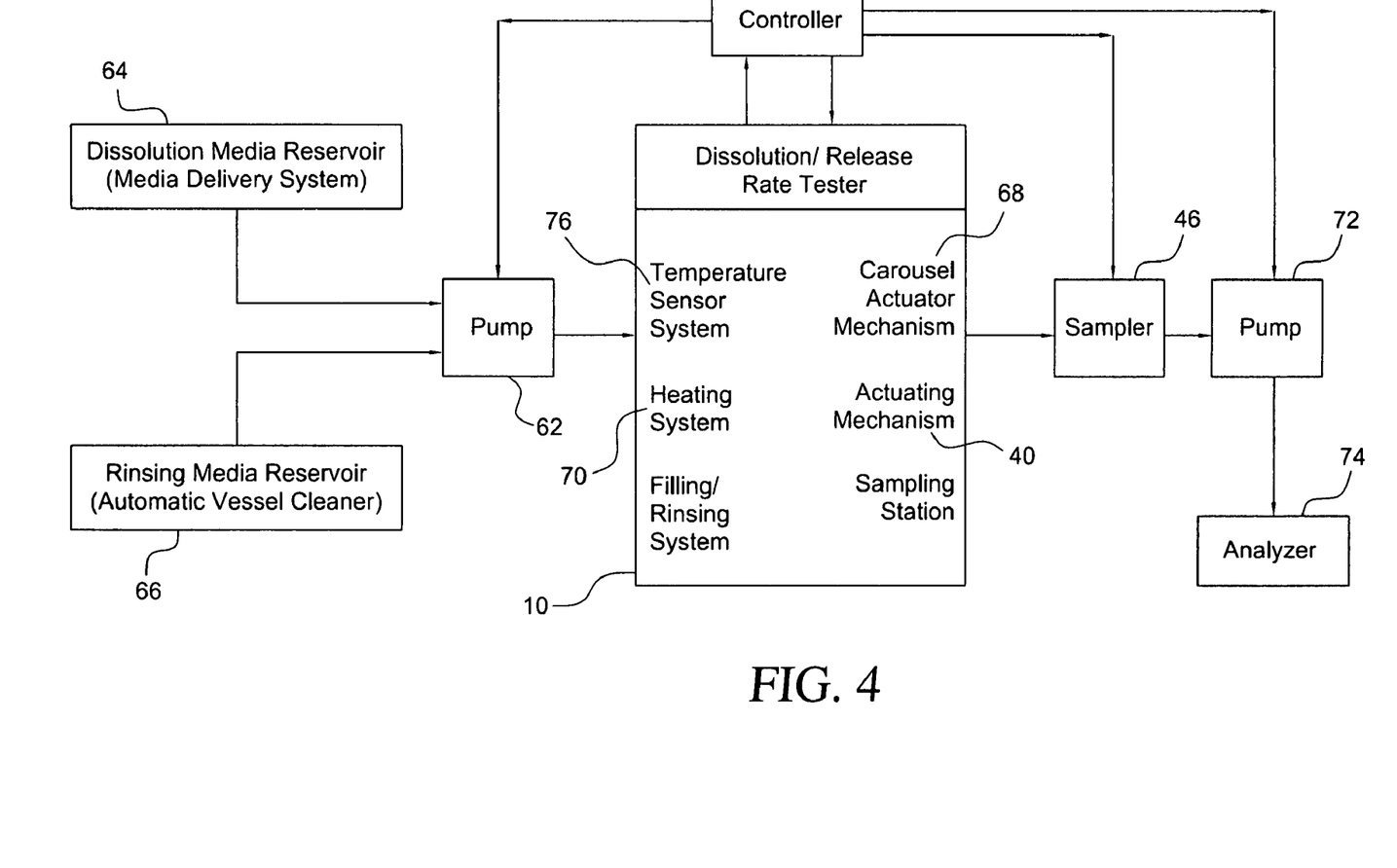
FIG. 4 is a schematic showing major parts of the release rate testing device in accordance with the invention.

Referring now to FIG. 4, a schematic of the system including the device 10 in accordance with the invention is shown. Device 10 defines the filling/rinsing station and the sampling station. A controller 60 is provided to control the entire release rate testing process. Controller 60 controls a pump 62 which has fluid connections to a reservoir of dissolution media 64 and a reservoir of rinsing media 66, which may be resident or part of an automatic vessel cleaner. These fluid connections provide for independent fluid paths from both the dissolution media reservoir 64 and the rinsing media reservoir 66 to the delivery nozzles 50. Fluid connections to a waste reservoir into which the rinsing fluid is directed after use for rinsing the test tubes is also provided, but not shown. Controller 60 also controls several mechanisms associated with, included in, integrated into or incorporated into the device 10, including actuating mechanism 40, a carousel rotation actuator 68 and a heating system 70. Carousel rotation actuator 68 controls the rotation of the carousel members 20. Heating system 70 controls the application of heat to the carousel members 20 and/or the pockets 26 defined thereby to heat the test tubes when retained in the pockets 26. Controller 60 also controls the sample collector 46 and a pump 72 connected to or integrated into the sample collector 46 which coordinate in the collection of samples from the sample probes 36 and forwarding of such samples to an analyzer 74. Controller 60 is connected to a temperature sensor system 76 associated with the carousel members 20 of the device 10 in order to receive temperature readings relating to the temperature of the test tubes in the pockets 26 of the carousel members 20.

In a non-limiting method for using the device and system described above and illustrated in the drawings, the first step is to set-up the device, which involves mounting delivery nozzles 50 on the plate 48, making the fluid connections between the delivery nozzles 50 and the pump 62, connecting the sample probes 36 to the sample collector 46, filling the reservoirs 64, 66, and other various preparatory steps.

The system is initiated and the controller 60 causes the actuating mechanism 40 to move the dipping arm into an elevated, home position via movement of the cross member 38 upward. The upward movement of the cross member 38 causes the upward movement of the cross member 52 and thus the filling and rinsing arm to an elevated, home position. With both the dipping arm and the filling and rinsing arm in elevated positions, test tubes are inserted into the carousel members 20 and the test method selected. Controller 60 initiates heating of the test tubes via heating system 70 and monitors the temperature provided by temperature sensor system 76 until the temperature reaches the temperature desired for the selected test method, i.e., 37° C.

Once the desired operational temperature is reached, controller 60 directs the actuating mechanism 40 to move the dipping arm downward to the lowest position causing the filling and rinsing arm to be moved to the lowest position with the delivery nozzles over or partially inside of the test tubes in the filling station. Controller 60 then directs pump 62 to pump fluid from the dissolution media reservoir 64 into the test tubes in the filling station (for the purpose of this explanation of a use of the invention, these test tubes are designated 1-12 and are one-half of the test tubes received in carousel members 20). This may entail directing a media delivery system to direct the dissolution or test media from the reservoir 64 into the test tubes.

Controller 60 then monitors the temperature of the test tubes (in particular, those including dissolution media) until it reaches a desired temperature, again for example 37° C. An audible indication or signal can be provided when this occurs. At this time, controller 60 controls actuating mechanism to move the dipping arm upward and thus the rinsing and filling arm upward until no part of the device 10 is present in the carousel members 20. Controller 60 then directs carousel rotation actuator 68 to rotate the carousel members 20 a rotation of about 180°, first disengaging the locking mechanism which prevents unintentional rotation of the carousel members 20. This brings test tubes 1-12 from the filling/rinsing station into the dipping station and the remaining test tubes, designated 13-24, from the dipping station into the rinsing/filling station. Samples are then loaded into the sample probes 36 and attached to the dipping shafts 32 and the actual test is ready to begin.

Controller 60 directs actuating mechanism 40 to move the dipping arm downward to a position in which the sample probes 36 are situated in the test tubes (those designated 1-12). Downward movement of the dipping arm causes the filling and rinsing arm to be moved downward with the delivery nozzles 50 over or partially inside of the test tubes in the filling station (those designated 13-24). Controller 60 then initiates a dipping stage in which it waits for an optional hold time (without any vertical movement of the dipping bars) and then dips the sample probes 36. Dipping involves the actuating mechanism 40 moving the cross member 38 up and down such that the sample holder retaining members 28 move along the pins 54 between the cross member 52 and the stops 56. The cross member 52 is not intentionally moved upward.

During the dipping stage, controller 60 directs pump 62 to pump fluid from the dissolution media reservoir 64 into the test tubes in the filling station (the test tubes designated 13-24). This may entail directing a media delivery system to direct the dissolution or test media from the reservoir 64 into the test tubes. This may occur about 20 minutes, or any other user-defined time, before the carousel members 20 are to be rotated. However this period of time may be set and adjusted as designed to prevent the dissolution media from evaporating prior to the dipping stage, since such evaporation may adversely affect the release rate testing.

When the dipping stage is complete, controller 60 directs actuating mechanism 40 to move the dipping arm upward and thus the rinsing and filling arm upward until no part of the device 10 is present in the carousel members 20. If the test is not concluded, controller 60 directs carousel rotation actuator 68 to rotate the carousel members 20 a rotation of about 180°, first disengaging the locking mechanism which prevents unintentional rotation of the carousel members 20. This moves test tubes 1-12 from the dipping station into the filling/rinsing station and test tubes 13-24 from the rinsing/filling station into the dipping station.

The test continues with controller 60 directing actuating mechanism 40 to move the dipping arm downward to a position in which the sample probes 36 are situated in the test tubes now in the dipping station (those designated 13-24). Downward movement of the dipping arm causes the filling and rinsing arm to be moved downward with the delivery nozzles 50 over or partially inside of the test tubes in the filling rinsing station (those designated 1-12). Controller 60 then initiates a dipping stage as described above.

Controller 60 also initiates a rinsing stage in which test tubes 1-12 in the rinsing/filling station are vacuumed out and rinsed. This entails directing pump 62 to pump fluid from the rinsing media reservoir 66 into the test tubes 1-12 through delivery nozzles 50 and vacuuming any fluid from the test tubes, both of which may be accomplished via an automatic vessel cleaner.

If after a dipping stage, the test is concludes, controller 60 causes actuating mechanism 40 to move dipping arm to its elevated, home position, causing filling and rinsing arm to also move to its elevated, home position.

Another apparatus preferred or required for the release rate testing is a syringe pump which withdraws samples from the sample probes 36. Such a syringe pump can be associated with the sample collector 46

The foregoing is one possible method for using the device in accordance with the invention. It being understood that other method for using the device are of course possible and envisioned to be within the scope and spirit of the invention.

While particular embodiments of the invention have been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

We claim:

1. A pharmaceutical product release rate testing device, comprising:
   a base;
   at least one carousel member rotatably mounted on said base, each of said at least one carousel member including a plurality of test tube pockets each adapted to receive a test tube fillable with test media;
   a dipping mechanism for dipping that dips samples of the pharmaceutical product to be tested into the test tubes when present in said test tube pockets and filled with test media, said dipping mechanism comprising a dipping arm coupled to said base and movable vertically relative to said at least one carousel member, said dipping arm being arranged to enable samples of the pharmaceutical product being tested to be dipped into test tubes when present in a first set of said test tube pockets and filled with test media;
   an analyzer unit that measures rate of dissolution of the pharmaceutical product in the test media after said dipping mechanism has dipped the samples of the pharmaceutical product into the test tubes tilled with the test media; and
   a filling/rinsing arm coupled to said base and movable vertically relative to said at least one carousel member, said filling/rinsing arm being arranged to rinse test tubes when present in a second set of said test tube pockets and fill test tubes with test media when present in said second set of test tube pockets,
   said first and second sets of said test tubes being different than one another such that both dipping of samples and rinsing or filling of test tubes can be performed simultaneously.

2. The device of claim 1, further comprising a heating system that applies heat to said at least one carousel member, a temperature sensor system that obtains temperature readings related to the temperature of test tubes when present in said pockets of said at least one carousel member and a controller coupled to said heating system and said temperature sensor system and that controls heating of the test tubes when present in said pockets.

3. The device of claim 1, wherein said at least one carousel member comprises a plurality of carousel members.

4. The device of claim 1, wherein said at least one carousel member comprises two carousel members arranged side by side on said base.

5. The device of claim 1, wherein said dipping arm is arranged to align with said first set of said pockets and said filling/rinsing arm is arranged to align with said second set of said pockets when said dipping arm aligns with said first set of said pockets.

6. The device of claim 1, wherein said at least one carousel member has a substantially cylindrical form and defines said pockets on an outer periphery, said first set of said pockets extending over a 180° segment and said second set of said pockets extending over the other 180° segment.

7. The device of claim 5, further comprising a rotation mechanism that rotates said at least one carousel member such that each of said first and second sets of said pockets is alternatingly in alignment with said dipping arm and in alignment with said filling/rinsing arm.

8. The device of claim 1, further comprising a mechanism that coordinates vertical movement of said dipping arm and vertical movement of said filling/rinsing arm.

9. The device of claim 1, wherein said dipping arm includes at least one semi-circular sample holder retaining member and dipping bars mounted to said sample holder retaining member.

10. The device of claim 1, further comprising an actuating mechanism that vertically moving moves said dipping arm between different vertical positions including a position in which the samples to be tested are dipped into the test tubes when present in said first set of pockets and filled with test media and a position in which the samples are over said at least one carousel member to enable said at least one carousel member to be rotated.

11. The device of claim 1, further comprising a rotation mechanism for rotating said at least one carousel member such that each of said first and second sets of said pockets is alternatingly in operative engagement with said dipping arm and in operative engagement with said filling/rinsing arm.

12. The device of claim 1, further comprising an actuating mechanism for vertically moving said dipping arm and said rinsing/filling arm between different vertical positions.

13. A device for managing dissolution of samples of pharmaceutical product into test media in test tubes and handling of the test tubes such that a rate of dissolution of the pharmaceutical product in the test media can be measured by an analyzer, the device comprising:
    a base;
    at least one carousel member rotatably mounted on said base, each of said at least one carousel member including a plurality of test tube pockets each adapted to receive a test tube fillable with test media;
    a dipping mechanism that dips samples of the pharmaceutical product to be tested into the test tubes when present in said pockets and filled with test media, said dipping mechanism being arranged to align with a first set of said pockets of said at least one carousel member, said dipping mechanism comprising a dipping arm coupled to said base and movable vertically relative to said at least one carousel member, said dipping arm being arranged to enable samples of the pharmaceutical product being tested to be dipped into test tubes when present in said first set of said pockets and filled with test media; and
    a filling/rinsing mechanism aligning with a second set of said pockets of said at least one carousel member when said first set of said pockets aligns with said dipping mechanism, said filling/rinsing mechanism comprising a filling/rinsing arm coupled to said base and movable vertically relative to said at least one carousel member, said filling/rinsing arm being arranged to fill test tubes with test media when present in said second set of said pockets or rinse test tubes when present in said second set of said pockets,
    said first and second sets of said test tube pockets being different than one another such that both dipping of samples and rinsing or filling of test tubes can be performed simultaneously.

14. The device of claim 13, wherein said at least one carousel member has a substantially cylindrical form and defines said pockets on an outer periphery, said first set of said pockets extending over a 180° segment and said second set of said pockets extending over the other 180° segment.

15. The device of claim 13, further comprising a rotation mechanism that rotates said at least one carousel member such that each of said first and second sets of said pockets is alternatingly in alignment with said dipping arm and in alignment with said filling/rinsing arm.

16. The device of claim 13, further comprising a mechanism that coordinates vertical movement of said dipping arm and vertical movement of said filling/rinsing arm.

* * * * *

UNITED STATES PATENT AND TRADEMARK OFFICE
CERTIFICATE OF CORRECTION

PATENT NO. : 7,585,465 B2 Page 1 of 1
APPLICATION NO. : 11/453634
DATED : September 8, 2009
INVENTOR(S) : Luke Lee et al.

It is certified that error appears in the above-identified patent and that said Letters Patent is hereby corrected as shown below:

Column 9, line 33, change "tilled" to --filled--.

Signed and Sealed this

Twenty-seventh Day of October, 2009

David J. Kappos
*Director of the United States Patent and Trademark Office*

UNITED STATES PATENT AND TRADEMARK OFFICE
CERTIFICATE OF CORRECTION

PATENT NO. : 7,585,465 B2  Page 1 of 1
APPLICATION NO. : 11/453634
DATED : September 8, 2009
INVENTOR(S) : Lee et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 424 days.

Signed and Sealed this

Fourteenth Day of December, 2010

David J. Kappos
*Director of the United States Patent and Trademark Office*